(12) United States Patent
Jones et al.

(10) Patent No.: US 7,078,058 B2
(45) Date of Patent: Jul. 18, 2006

(54) CORTICOSTEROID-CONTAINING PHARMACEUTICAL COMPOSITION

(75) Inventors: Julie Irene Jones, Harpenden (GB); Anthony Richard Baker, West Horsley (GB); Neil Graham Halls, Glen Waverley (AU); Peter Watmough, Grimsby (GB); Peter Marriott, Grimsby (GB)

(73) Assignee: Connetics Australia Pty Ltd, Rowville (AU)

( * ) Notice: Subject to any disclaimer, the term of this patent is extended or adjusted under 35 U.S.C. 154(b) by 449 days.

(21) Appl. No.: 10/256,754

(22) Filed: Sep. 27, 2002

(65) Prior Publication Data

US 2003/0118511 A1    Jun. 26, 2003

Related U.S. Application Data

(60) Continuation of application No. 09/624,473, filed on Jul. 24, 2000, now abandoned, and a division of application No. 08/913,144, filed on Jan. 12, 1998, now Pat. No. 6,126,920.

(60) Provisional application No. PCT/GB96/00490, filed on Mar. 1, 1996.

(30) Foreign Application Priority Data

Mar. 3, 1995  (GB) ................................. 9504265.1

(51) Int. Cl.
| | |
|---|---|
| *A61K 9/00* | (2006.01) |
| *A61K 9/16* | (2006.01) |
| *A61K 9/50* | (2006.01) |
| *A61L 9/04* | (2006.01) |

(52) U.S. Cl. .......................... 424/495; 424/43; 424/45
(58) Field of Classification Search ................ 424/495, 424/45, 43

See application file for complete search history.

(56) References Cited

U.S. PATENT DOCUMENTS

| 4,018,918 A | 4/1977 | Ayer et al. .............. 424/240 |
| 4,882,182 A | 11/1989 | Halls et al. |
| 4,888,354 A | 12/1989 | Chang et al. |
| 4,915,934 A | 4/1990 | Tomlinson |
| 4,981,678 A | 1/1991 | Tomlinson |
| 5,516,504 A | 5/1996 | Tomlinson |
| 5,783,202 A | 7/1998 | Tomlinson et al. |
| 5,935,554 A | 8/1999 | Tomlinson |
| 6,211,250 B1 | 4/2001 | Tomlinson et al. |
| 6,231,875 B1 | 5/2001 | Sun et al. |
| 6,267,949 B1 | 7/2001 | Halls |
| 6,284,234 B1 | 9/2001 | Niemiec et al. |
| 6,383,471 B1 | 5/2002 | Chen et al. |
| 6,419,913 B1 | 7/2002 | Niemiec et al. |

FOREIGN PATENT DOCUMENTS

| EP | 0 331489 A2 | 9/1989 |
| EP | 0423695 A3 | 10/1991 |
| EP | 0 160051 B1 | 1/1992 |
| EP | 1 070752 A2 | 1/2001 |
| WO | WO85/01876 | 5/1985 |
| WO | WO 86/00196 | 1/1986 |
| WO | WO 88/04896 | 7/1988 |
| WO | WO 92/04419 | 3/1992 |
| WO | WO 94/16732 | 8/1994 |
| WO | WO 98/23291 | 6/1998 |
| WO | WO 98/52525 | 11/1998 |
| WO | WO 99/20250 | 4/1999 |
| WO | WO 99/53923 | 10/1999 |
| WO | WO 00/15193 | 3/2000 |
| WO | WO 00/66172 | 11/2000 |

OTHER PUBLICATIONS

Yip and Po "The stability of betamethasone-17-valerate in semi-solid bases" *J. Pharm. Pharmacol.* 31, 400-402 (1979).

Timmens, P. and Gray, E., "The degradation of triamcinolone acetonide in aqueous solution: influence of the cyclic ketal function," *J. Pharm. Pharmacol.*, 35:175-177 (1983).

Woodford, R. and Barry, B. W., "Bioavailability and Activity of Topical Corticosteroids from a Novel Drug Delivery System, the Aerosol Quick-Break Foam," *J. Pharm. Sci.*, 66:99-103 (1977).

Albert Zorko Abram and Roderick Peter John Tomlinson, Mousses, Chapter 19, pp. 221-232, Soltec Research Pty Ltd., Rowville, Victoria, Australia, Jun. 2001.

*Primary Examiner*—San-Ming Hui
(74) *Attorney, Agent, or Firm*—Townsend and Townsend and Crew LLP

(57) ABSTRACT

A foamable pharmaceutical composition comprising a corticosteroid, a quick-break foaming agent, a propellant and a buffering agent, sufficient to buffer the composition to within the range of pH 3.0 to 6.0 is disclosed. The quick-break foaming agent typically comprises an aliphatic alcohol, water, a fatty alcohol and a surface active agent. Due to the nature of the compositions of the invention, they are especially well-suited for use in the treatment of various skin diseases, and in particular, in the treatment of scalp psoriasis.

1 Claim, No Drawings

CORTICOSTEROID-CONTAINING PHARMACEUTICAL COMPOSITION

CROSS REFERENCE TO RELATED APPLICATIONS AND CLAIM FOR FOREIGN PRIORITY

This application is a continuation of U.S. patent application Ser. No. 09/624,473 (now abandoned), filed Jul. 24, 2000 as a divisional of U.S. patent application Ser. No. 08/913,144 (now U.S. Pat. No. 6,126,920), filed Jan. 12, 1998 as a §371 United States National Phase filing of PCT/GB96/00490 (expired), filed Mar. 1, 1996 claiming priority from GB 9504265.1, filed Mar. 3, 1995. The entire contents of each of the earlier applications is incorporated herein by reference.

FIELD OF THE INVENTION

The present invention relates to an improved pharmaceutical composition for the topical administration of corticosteroid-active substances to the skin of a subject.

BACKGROUND OF THE INVENTION

Corticosteroids, particularly in the form of ester compounds, are used, inter alia, in the treatment of skin diseases in humans, such as, for example, eczema, infantile eczema, atopic dermatitis, dermatitis herpetiformis, contact dermatitis, seborrheic dermatitis, neurodermatitis, psoriasis and intertrigo. Formulations containing such active substances have conventionally been applied to the skin site in the form of alcoholic solution, lotions or creams. However, there is a high degree of ineffectiveness with such formulations. Lotions and creams are generally too viscous o allow efficient penetration of the active ingredient to the epidermis, and solution have a tendency to evaporate before penetrating the epidermis. In addition, convention cream bases are irritating to the ski, particularly over the often long exposure that is required, and the fluidity of lotions often makes the physical application difficult to control. Moreover, it is necessary to rub such formulations into the target site to improve the penetration of the active substance into the epidermis, an action which itself produces irritation.

There has therefore been a very real need in the treatment of skin disorders requiring treatment with corticosteroids for improved formulations which target the most effective corticosteroid to the skin site with improved delivery of the active substance, with decreased inconvenience and irritation, and increased ease of use for the patient.

SUMMARY OF THE INVENTION

The present invention provides an improved composition which addresses these needs.

In one embodiment, the present invention provides a foamable pharmaceutical composition comprising a corticosteroid active substance, a quick-break foaming agent, a propellant and a buffering agent.

Such a composition is applied to the skin site (after foaming) as a foam which is a thermophobic (heat sensitive) quick-break foam. On application to the skin, the composition is initially in the form of a mousse-like foam. The quick-break foam slowly breaks down at the skin temperature to a liquid to allow the alcohol and active substance to saturate the treatment site. Such a system provides enhanced penetration of the alcohol and active substance through the epidermis. Because the composition is supplied as a mousse, the semi-rigid behavior of the composite makes it easier to handle and physically control. The foamed composition, when applied, provides a thick ball of foam which disintegrates easily when spread, allowing proper coverage of the skin site to be treated without premature evaporation of the solvent. It has been found important to include a buffering agent in the composition to stabilize the active isomer of the corticosteroid active substance in the complex foamable composition, otherwise the complex interactions within the foamable composition may result in the instability of the more active isomer.

DETAILED DESCRIPTION OF THE INVENTION

Use of a quick-break foaming agent is required in the present invention. Such agents are known. Suitable quick-break foaming agents in the present invention are those described in Australian Patent Number 463216 and Published International Patent Application WO 85/01876. It is generally preferred that the quick-breaking foaming agent comprises an aliphatic alcohol, water, a fatty alcohol and a surface active agent. Particularly preferred is a quick-break foaming agent having the following composition:
  (a) an aliphatic alcohol, preferably in amounts of 40–90% w/w composition, more preferably, 55–70% w/w, and especially preferred, 57–59% w/w;
  (b) water, preferably in amounts of 10–40% w/w;
  (c) at least one fatty alcohol, preferably in amounts of 0.5–10% w/w; and
  (d) a surface active agent, preferably an ethoxylated sorbitan ester (as emulsified), typically in amounts of 0.1–15% w/w.

In the quick-break foaming agent, the fatty alcohol may be chosen from, for example, cetyl, stearyl, lauryl, myristyl and palmityl alcohols and mixtures of two or more thereof. Mixtures of cetyl alcohol and a stearyl alcohol such as octadecan-1-ol have been found to be particularly preferred; the ratio between these two components may be adjusted to maintain foam viscosity throughout the broadest possible temperature range. In this situation, the stearyl alcohol maintains the viscosity at temperatures above 20° C. whilst cetyl alcohol maintains the viscosity below 20° C.

The aliphatic alcohol may preferably be chosen from methyl, ethyl, isopropyl and butyl alcohols, and mixtures of two or more thereof. Ethanol has been found to be particularly preferred.

Surface active agents utilized in the quick-break foaming agent may preferably be chosen from ethoxylated sorbitan stearate, palmitate, oleate, nonyl phenol ethoxylates and fatty alcohol ethoxylates, and mixtures of two or more thereof. Thus, for example, Polysorbate 60 (a mixture of partial stearic esters of sorbitol and its anhydrides copolymerized with approximately 20 moles of ethylene oxide for each mole of sorbitol and its anhydrides) has been found to be particularly preferred. The surface active agent enhances the fatty alcohol solubility in the system and enhances foam formation.

The propellant used may be chosen from conventional aerosol propellants. Thus, one may select the propellant from propane, butane, dichloro difluoro methane, dichloro tetrafluoro ethane, octafluoro cyclobutane, and mixture s of two or more thereof. It is necessary to select a propellant most compatible with the entire system. It is particularly preferred that the propellant be present in amounts preferably of 3–30% w/w, more preferably, 3–10% w/w, and most preferably, 3–5% w/w. The maximum level of propellant will be determined as the amount miscible with the utilized water/aliphatic alcohol ratio. In addition to acting as a propellant, the propellant will also act as a solvent for the fatty acids and active substances in the aqueous/alcoholic system.

It is possible that other additives may be used. Thus, it is preferred to add a humectant to reduce the drying effects of the aqueous aliphatic alcohol. Such a humectant may preferably be present in an amount of 0.1–10% w/w and more preferably 0.5–3.0% w/w. To is particularly preferred that the humectant be propylene glycol, but other humectants such as glycerine, panthenol and sorbitol may also be use.

The composition of the present invention may be used to deliver corticosteroid compounds which have utility in the topical treatment of skin disorders. Thus, for example, the composition of the present invention may be used to deliver the following topically-effective corticosteroid:

| | |
|---|---|
| alclometasone dipropionate | fluclorolone acetonide |
| amcinonide | fluocinolone acetonide |
| beclomethasone dipropionate | fluocinonide |
| betamethasone benzoate | fluocoritin butyl |
| betamethasone dipropionate | fluocortolone preparations |
| betamethasone valerate | fluprednidene acetate |
| budesonide | flurandrenolone |
| clobetasol propionate | halcinonide |
| clobetasol butyrate | hydrocortisone |
| desonide | hydrocortisone butyrate |
| desoxymethasone | methylprednisolone acetate |
| diflucortolone valerate | mometasone furoate |
| flumethasone pivalate | triamcinolone acetonide |
| and pharmacologically effective mixtures thereof | |

Compositions according to the invention are especially advantageous for the topical administration to the skin of human subjects of betamethasone and its derivatives, such as betamethasone benzoate, betamethasone dipropionate and betamethasone valerate. It is particularly preferred to use the valerate ester, especially in the treatment of psoriasis.

The corticosteroid active substance is preferably present in an amount o 0.01–1.0% w/w and more preferably, 0.05–0.2% w/w.

In view of the complexity of the composition, it has been found that unexpectedly, in order to ensure stability of the active isomer of the corticosteroid in the composition, and thus to ensure delivery of the most active isomer to the epidermis, it is necessary to buffer the composition by including a suitable buffering agent. Suitable buffering agents are acetic acid/sodium acetate, citric acid/sodium citrate and phosphoric acid/sodium phosphate, and it is desirable generally to buffer the composition to pH 3.0 to 6.0 and preferably, to pH 4.0–5.0. To this end, the buffering agent may preferably be present in an amount of 0.01–1.0% w/w and more preferably 0.05%–0.2% w/w. It is particularly preferred to use a citrate buffer system, and more preferably, anhydrous citric acid/potassium citrate, to buffer the composition to pH 4.5, when betamethasone valerate is used as the active substance; in this case, citrate buffering stabilizes the more active 17-valerate ester over the less active 21-valerate ester in the complex composition and ensures that the most effective form of the active substance is efficiently delivered to the epidermis.

Preparation of the composition may be affected by conventional means, so as to produce a homogeneous solution of fatty alcohol(s) or wax(es), in the alcohol/water base. The relative proportions of the fatty alcohol(s), water/aliphatic alcohol and propellant are conveniently controlled according to conventional means so as o provide a homogeneous clear solution and so as to allow the formation of a suitable quick-break foam. Generally speaking, the fatty alcohol(s), surface active agent, aliphatic alcohol and humectant (when present) are preferably mixed together with the corticosteroid active substance to produce and "alcohol phase". An "aqueous phase" is preferably produced by mixing the buffering agent and water. These phases are then mixed, preferably in the final container, in the required amounts. The propellant is then added under pressure to produce he composition according to the present invention.

In the case of betamethasone valerate, for example, it is particularly preferred to use a composition comprising cetyl alcohol and octadecan-1-ol as fatty alcohols, together with Polysorbate 60 surface active agent, with purified water and ethanol as the aliphatic alcohol. The system is preferably buffered with anhydrous citric acid potassium citrate and the propellant is preferably butane/propane. It is generally preferred to choose the proportion of the components to achieve a fixed pressure in the container of around 50–70 psi.

The composition of the present invention may be contained in and dispensed from, a container capable of withstanding the pressure of the propellant gas and having an appropriate valve/nozzle for dispensing the composition as a foam under pressure. If the container is made of metal material likely to suffer corrosion under the action of the composition, the composition may include a corrosion inhibitor as an additive. Thus, the present of a corrosion inhibitor may be necessary if the container is made of tin plate. Suitable corrosion inhibitors include organic acid salts, preferably chosen from sorbic acid, benzoic acid, sodium benzoate and potassium sorbate. If used, the corrosion inhibitor maybe present in amounts of 0.1–15% w/w and more preferably, 0.1–3.0% w/w. In the present invention, aluminum cans are preferred as containers, particularly when utilizing the above-mentioned composition for betamethasone valerate as the corticosteroid active substance; in this case, there is no corrosion problem and there is no need of the inclusion of a corrosion inhibiting agent.

In use, the composition is sprayed, producing a semi-solid (i.e. a foam or mousse) that is suitable for the topical application to the scalp. On application, heat from the skin causes the mousse to break down into liquid form, thus releasing the aliphatic alcohol and corticosteroid active substance which penetrate the skin site, leaving a low amount of residue, many times lower than those obtained when delivering active ingredient from a cream base. This route of administration facilitates the ease of specific local applications, and the composition according to the present invention provides a convenient, controllable and efficient vehicle for delivering active substance to the skin. This gives greater physical control compared to conventional topical corticosteroid formulations, minimizes rubbing of the target site and allows the alcoholic vehicle to penetrate the skin to deliver the active ingredient where it will have the greatest effect.

The composition of the present invention may be used in treating skin diseases that are conventionally treated with corticosteroid active substances. Thus, the composition may be use in the treatment of, inter alia, eczema, infantile eczema, atopic dermatitis, dermatitis herpetiformis, contact dermatitis, seborrheic dermatitis, neurodermatitis, psoriasis and intertrigo. The composition is especially useful in the treatment of scalp psoriasis in human subjects.

The principals of the present invention are illustrated below by means of the following non-limiting example.

A betamethasone valerate formulation having the following composition was prepared:

| Ingredient | % w/w |
| --- | --- |
| betamethasone valerate | .12 |
| cetyl alcohol BP | 1.10 |
| octadecan-1-ol BP | 0.50 |
| Polysorbate 60 BP | 0.4. |
| ethanol | 57.79 |
| purified water | 33.69 |
| propylene glycol BP | 2.00 |
| citric acid anhydrous BP | 0.073 |
| potassium citrate | 0.027 |
| butane/propane | 4.30 |
| | 100.000 |

Alcoholic Phase

Cetyl alcohol (HYFATOL 1698, Efkay Chemicals Limited, London, England), octadecan-1-ol (HYFATOL 1898, Efkay Chemicals Limited, London, England), Polysorbate 60 (CRILLET 3, Croda Chemicals, North Humberside, England) and ethanol in the appropriate proportions were mixed and heated to about 45° C., with continuous stirring until the mix became clear. Betamethasone valerate BP (Roussel Uclaf, Virtolaye, France) was slowly transferred into the mix, again with continuous stirring until the mix became clear.

Aqueous Phase

Purified water was separately heated to 45° C. and anhydrous citric acid BP and potassium citrate BP transferred to the water, with continuous stirring until dissolved.

The alcoholic and aqueous phases were each filtered through 75μ screens and the required weights filled into a can (epoxy lined aluminum) at room temperature. After attaching a valve, the butane/propane propellant (Propellant P&)) was added to the mix in the can to the required weight, and an actuator added to the valve.

The composition, on being sprayed from the can onto the skin, produces a thermophobic foam which breaks down under heating from the skin to release the active ingredient to the epidermis. The presence of the citrate buffer stabilizes the 17-valerate configuration of the betamethasone valerate over the less active 21-valerate configuration, thus producing a composition which efficaciously delivers the active ingredient to the epidermis and which is particularly suitable for the treatment of psoriasis, especially scalp psoriasis.

We claim:

1. A foamable pharmaceutical composition adapted for topical administration having the following composition:

| | % w/w |
| --- | --- |
| Betamethasone Valerate | 0.120 |
| Cetyl Alcohol BP | 1.100 |
| Octadecan-1-ol BP | 0.500 |
| Polysorbate 60 BP | 0.400 |
| Ethanol | 57.790 |
| Purified Water | 33.690 |
| Propylene Glycol BP | 2.000 |
| Citric Acid Anhydrous BP | 0.073 |
| Potassium Citrate | 0.027 |
| Butane/Propane | 4.300 |
| | 100.000. |

* * * * *